United States Patent
Schmitt

(10) Patent No.: US 7,432,807 B2
(45) Date of Patent: Oct. 7, 2008

(54) METHOD FOR PROTECTING A MEDICAL DEVICE

(75) Inventor: Thomas Schmitt, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 300 days.

(21) Appl. No.: 11/311,593

(22) Filed: Dec. 15, 2005

(65) Prior Publication Data

US 2006/0132991 A1   Jun. 22, 2006

(30) Foreign Application Priority Data

Dec. 17, 2004   (DE) .................... 10 2004 060 930

(51) Int. Cl.
*G08B 13/14* (2006.01)

(52) U.S. Cl. ..................... 340/568.1; 340/539.13; 340/572.1; 340/686.1

(58) Field of Classification Search ............. 340/572.1, 340/539.13, 568.1, 686.1, 686.6, 539.15, 340/539.21, 539.23

See application file for complete search history.

(56) References Cited

U.S. PATENT DOCUMENTS 6,614,350 B1 * 9/2003 Lunsford et al. ......... 340/572.1
2001/0020148 A1   9/2001 Sasse et al.

FOREIGN PATENT DOCUMENTS

| DE | 101 12 303 A1 | 10/2002 |
| GB | 2 381 110 A | 4/2003 |
| WO | WO 2004/008387 A1 | 1/2004 |

* cited by examiner

*Primary Examiner*—George A Bugg
*Assistant Examiner*—Travis R Hunnings

(57) ABSTRACT

A method is disclosed for protecting a medical device against unauthorized removal from a predefined location area. To this end the device to be protected and/or at least one further device in the predefined location area transmits protection signals. The protection signals transmitted by the device to be protected and/or the protection signals received by the device to be protected are then evaluated and a specific operating state of the device to be protected is activated as a function of a result of the evaluation. A corresponding system for protecting a medical device and a medical device for use with such a protection method or system is also described.

21 Claims, 2 Drawing Sheets

METHOD FOR PROTECTING A MEDICAL DEVICE

CROSS REFERENCE TO RELATED APPLICATIONS

This application claims priority to the German application No. 10 2004 060 930.6, filed Dec. 17, 2004 which is incorporated by reference herein in its entirety.

FIELD OF INVENTION

The invention relates to a method for protecting a medical device against unauthorized removal from a predefined location area, for example a specific work area. The invention also relates to a corresponding system for protecting a medical device and a medical device for use with such a protection method or system.

BACKGROUND OF INVENTION

As technology progresses increasingly complex and therefore more expensive devices are used in the medical field both for diagnosis and for patient treatment. This is also true in particular of mobile devices, which are not fixed in the examination room—for example by means of gantries, etc.—or which are not so large and heavy, for example like CT or MR devices, that they cannot be easily transported. A typical example of such a particularly expensive, mobile medical device is the increasingly used semiconductor X-ray detector. These devices can be used with a wide variety of X-ray devices, precisely because of their mobility. They can be used there to record X-ray data in digital form and to transmit the image data via a radio interface or when plugged into a base station via a cable connection to an RIS (Radiological Information System) or PACIS (Picture Archiving and Communication Information System). The images can then be further processed at different stations of the RIS or PACIS before being output and/or stored. Because of their high cost and easy transportability, such devices have now become a relatively popular target for criminality to order, with the theft of such specialist medical components being commissioned specifically, in order to sell the devices on in an appropriate black market. Relatively large medical institutions such as hospitals, etc. are particularly vulnerable to such thefts, as it is often easy to enter the examination areas disguised as nursing or maintenance personnel and remove the devices without authorization. Until now such institutions have only been monitored by local or door-based personnel but in many cases it is still easy to smuggle devices out.

Various electronic protection methods are however already available in the medical field.

US 2001/0020148 A1 discloses a method for using transponders to ensure that only authorized accessories can be used on a medical device. There is however no provision for protecting the devices against theft.

GB 2 381 110 A1 discloses a method, in which the location, occupancy and optionally the nature of use of beds or seat units, e.g. wheelchairs, can be controlled by a specialist, central monitoring unit, which can display current status or location. A theft may be discovered at an earlier stage in this manner. To prevent theft however, the central monitoring unit would have to be controlled by security personnel all the time.

WO 2004/008387 A1 also proposes tracking the "life" of medical products, specifically pharmaceutical products, using RIFD tags in their packaging or other containers or instruments such as syringes, catheters etc. and linking the products to specific information, such as date of manufacture, manufacturer, dosage, payment conditions, legal provisions, medical information, etc. This is intended to reduce the risk of incorrect use or even abuse of such products.

There are also monitoring methods to control the location of instruments of instrument parts during use for example using appropriate transponder technologies. For example DE 101 12 303 A1 sets out a method for the wireless detection of the movement of a medical instrument, for example a catheter, inside the body of a patient.

However none of these methods offers effect anti-theft protection for expensive medical devices.

SUMMARY OF INVENTION

One object of the present invention is therefore to create a method and a system for protecting a medical device, in particular a mobile X-ray detector, against unauthorized removal from a predefined location area, i.e. protection against theft or other unauthorized misappropriation, which can be implemented reliably yet with simple means and without personnel outlay.

This object is achieved by the claims.

The claimed system and protection method thereby provide for the device to be protected and/or at least one further device in the predefined location area in proximity to the device to be protected to emit protection signals. These further devices can for example be other medical devices having corresponding components to emit protection signals or specialist protection signal transmitters. The signals can thereby be transmitted via any communication channel. The protection signals transmitted by the device to be protected and/or the protection signals received by the device to be protected are then evaluated. Finally as a function of a result of the evaluation a specific operating state of the device to be protected is activated. For example if the device is no longer in the permitted area, it can be switched to an alarm state, in which an alarm signal is output. If the device is normally in a standby mode, in which the device cannot be used in the required manner, as in a lock-out circuit, in the event of a positive evaluation result—i.e. if the device is still within the predefined location area—the device can be released. Conversely it is also possible for the device in principle to be in a state, in which it can be used in the required manner, and to be switched to a lock-out operating state only if the result of the evaluation is negative. The claimed activation of the operating state as a function of the evaluation result also means that if the device is already in a released state for example and the result of the evaluation is positive, it remains in this operating state and is not switched to a lock-out operating state. Conversely the device remains blocked if it is already in a lock-out operating state and the result of the evaluation proves to be negative.

The permitted location area is a function on the one hand of where the other devices, with which the device to be protected exchanges signals, are located and the range of the communication channel used. A wireless communication channel is preferably used, having a range of several meters, so that the mobile device can be moved within an acceptable operating radius, for example within the entire department of a hospital. On the other hand the range should not be so great that there are security gaps. Particularly suitable transmission standards with an appropriate range are for example Bluetooth, W-LAN or DECT.

A corresponding system for protecting a mobile medical device requires either a transmit arrangement connected to the device to be protected itself, for example integrated in the device to be protected, for transmitting protection signals. Alternatively or additionally the device has a receive arrangement for receiving protection signals transmitted by the further devices in the predefined location area. The device to be protected is thereby preferably equipped both with the transmit arrangement and also with a corresponding receive arrangement, so that it can both transmit protection signals itself and receive protection signals from other devices. The system also requires a number of further devices to be disposed in the predefined location area, each also having a transmit arrangement for transmitting protection signals for the device to be protected and/or a receive arrangement for receiving protection signals from the device to be protected. The system must also comprise an evaluation unit, to evaluate the protection signals transmitted by the device to be protected and/or received by the device to be protected. An activation unit is also required in the device to be protected, for activating a specific operating state of the device to be protected as a function of the result of the evaluation.

A suitable medical device for the claimed protection method must therefore have a transmit arrangement for transmitting protection signals and/or a receive arrangement for receiving protection signals for use in such a protection method, in addition to the components required for its own deployment purposes. Said medical device must also have an evaluation unit to evaluate the protection signals received by the device to be protected. Alternatively or additionally the device can also have a transmit arrangement for forwarding received protection signals for example to a central protection arrangement and/or a receive arrangement for receiving an activation signal, for example from the central protection arrangement. The medical device also requires an activation unit for activating a specific operating state as a function of a result of the evaluation and/or a received activation signal.

The dependent claims respectively contain particularly advantageous embodiments and developments of the invention. The claimed system can thereby also be developed according to the method claims and vice versa. The claimed medical device can also be developed according to the method or system claims.

The protection signal preferably comprises an ID uniquely assigned to the transmitting device. Such an ID or identification code makes clear to the receiving device from which other device the protection signal originates. It is thereby possible for example for the further devices in the location area of the device to be protected and serving to protect the device to be protected to identify uniquely whether the protection signal is also transmitted by the device to be protected. Conversely the device to be protected can also determine accurately whether the received protection signals are transmitted by those devices provided to protect the device.

Such a unique device ID can for example be obtained on the basis of randomly occurring device features. For a detector for example the number of pixel errors in a specific column and/or line can be used to form a unique ID according to a specific rule. If the device features change over time, the unique device ID can also change. It is however essential that before it changes its ID the respective device gives notification of this to the other components serving to protect the device or a central protection arrangement, if one exists.

In the case of a method in which the device to be protected receives protection signals from other devices, to verify whether it is still in the predefined location area, the other devices can transmit protection signals independently, for example in a specific clock pulse. In a preferred variant however the device to be protected transmits prompt signals to the other devices, from which it wishes to receive a protection signal.

These devices then send a protection signal back. Such a prompt signal is thereby particularly preferably only transmitted to a group of specific, previously selected devices. It is then verified during the evaluation whether precisely these selected devices send their protection signals back.

It is thereby particularly advantageous if the device or devices, to which the prompt signal is transmitted, are selected according to a random principle. This makes it more difficult for potential thieves to record protection signals and send them back to a device to be protected that they intend to misappropriate, so that said device no longer identifies when it is removed from the location area.

The evaluation of the protection signals received by the device to be protected preferably includes a determination of a combination value based on the protection signals from a number of selected devices according to a specific combination rule. To this end the evaluation unit preferably has a combination unit, which determines the combination value according to a specific combination rule based on a number of protection signals received by the device to be protected.

The evaluation of the protection signals received by the device to be protected can also include a comparison of the combination value with a corresponding reference value. If only one protection signal is used for the evaluation, a comparison of a single protection signal with a corresponding reference value can be carried out correspondingly. Alternatively it is also possible to compare a number of protection signals respectively with individual reference values. To this end the evaluation unit has a comparison unit, to compare protection signals or combination values respectively with a reference value. The reference values can for example be stored in a memory unit of the device to be protected during an initialization procedure.

The protection signals can for example be evaluated directly in an evaluation unit in the device to be protected itself.

The device to be protected can however also send the received protection signals to a central protection arrangement, which evaluates the protection signals and releases the device to be protected for use and/or activates an alarm as a function of the result of the evaluation. To this end the device to be protected and/or the other devices must have a transmit arrangement for forwarding received protection signals.

As part of the system as a whole, the central protection arrangement must have a corresponding receive arrangement for receiving the forwarded protection signals and an evaluation unit for evaluating the protection signals. The central protection arrangement also requires a transmit arrangement, to send an activation signal, for example a release signal, to the device to be protected as a function of an evaluation result, for activating a specific operating state of the device to be protected. Additionally or alternatively the central protection arrangement can also have an alarm arrangement, for activating an alarm centrally as a function of the result of the evaluation.

Such a central protection arrangement can for example be a computer component implemented by means of software.

If a central protection arrangement is used, the device whose protection signals are used to determine a combination value can be selected centrally by the protection arrangement. To this end the central protection arrangement can forward a device information signal to the device to be protected, comprising information, for example the addresses, relating to the devices in the communication network used, whose protection signals are used to determine the combination value. Alternatively the central protection arrangement can also transmit the prompt signals itself. If a central protection arrangement is used, the reference values for comparison with the protection signals and/or combination values are preferably stored in a memory unit of the protection arrangement.

If the device to be protected itself has an evaluation unit, the central protection arrangement can then also send a reference value for comparison with a protection signal or a combination value of the different protection signals respectively to the device to be protected. It is also possible here for the combination rule to be transmitted at the same time, said combination rule being used by the device to be protected or its evaluation unit to determine the combination value on the basis of the received protection signals, to carry out the comparison with the reference value. The reference value and/or combination rule is/are preferably transmitted encrypted.

BRIEF DESCRIPTION OF THE DRAWINGS

The invention is described in more detail below based on exemplary embodiments with reference to the accompanying figures, in which.

DETAILED DESCRIPTION OF INVENTION

Figure 1:
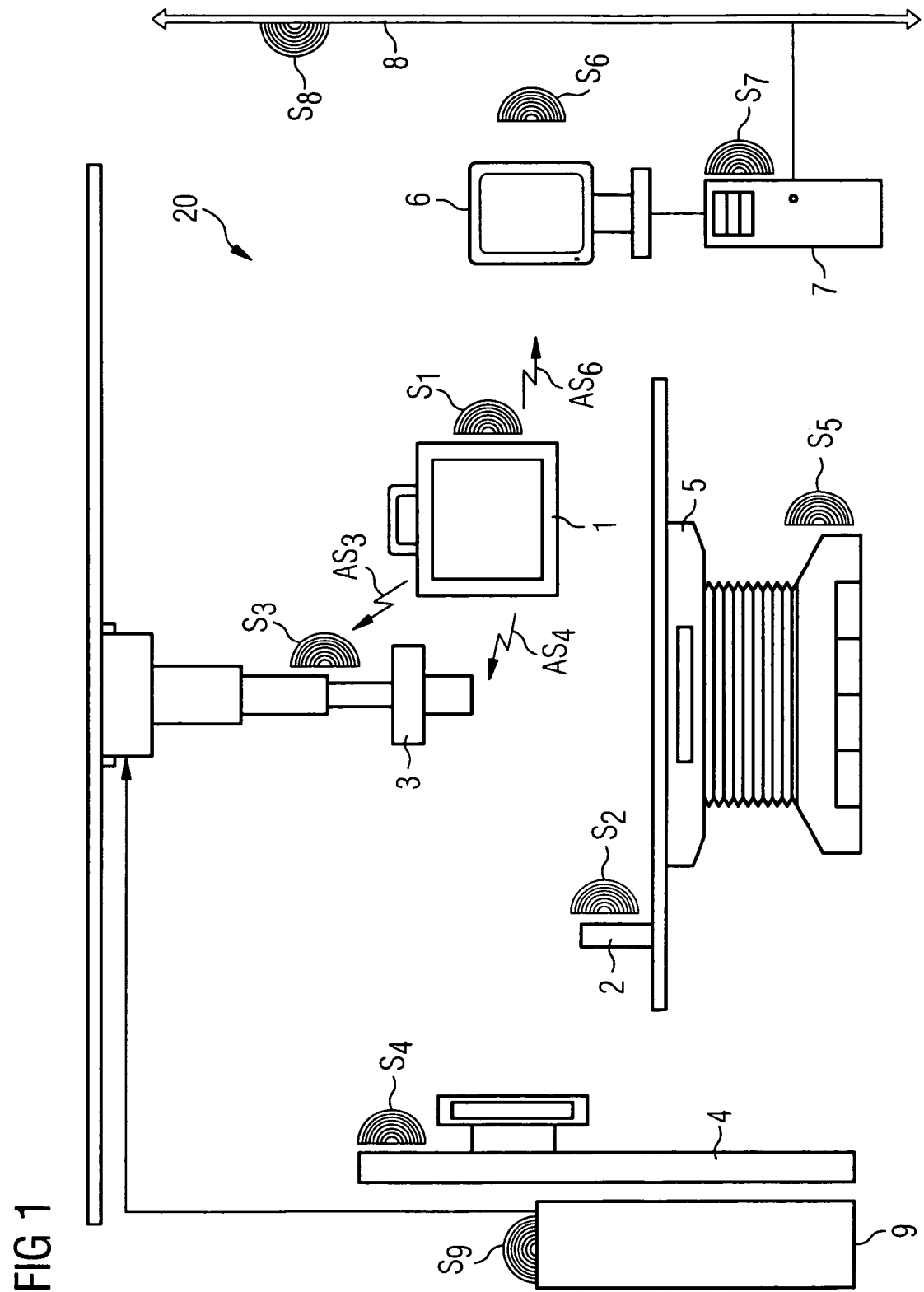
FIG. 1 shows a schematic diagram of a system for protecting a mobile digital X-ray detector.

FIG. 1 shows a schematic diagram of different devices and components generally present in an X-ray room. These devices include an examination table 5, in this instance a so-called Multix table 5, into which a mobile detector 1 can be integrated. Additional components 2, for example supports for a patient, screening materials, etc. can be used on this table 5. There is also a screen wall device 4 with a wall gantry in the examination room, into which the mobile X-ray detector 1 can also be inserted. An X-ray emitter 3 with an aperture stop is disposed in the center of the room on a ceiling gantry. The ceiling gantry can be used to move the X-ray emitter 3 into any position in the room, so that X-rays can be taken using the screen wall device 4, the Multix table 5 or even freely in the room using the mobile X-ray detector 1. An X-ray generator 9 supplies the X-ray emitter 3 with the necessary high voltage. There is also a so-called check monitor 6 directly in the examination room or separated from the X-ray room by means of an X-ray-absorbent wall. Operators can use this check monitor 6 to look immediately at the X-ray image taken in preview mode to check that the recordings are of good enough quality or if a new recording has to be made. The check monitor 6 is connected to an image processor 7, which is connected to a network bus 8 for connection to further components of an RIS or PACIS. All these devices and components 2, 3, 4, 5, 6, 7, 8, 9 are elements of the protection system 20, to protect the X-ray detector 1 and—like the X-ray detector 1 to be protected itself—each have a transmit/receive unit 11.

Figure 2:
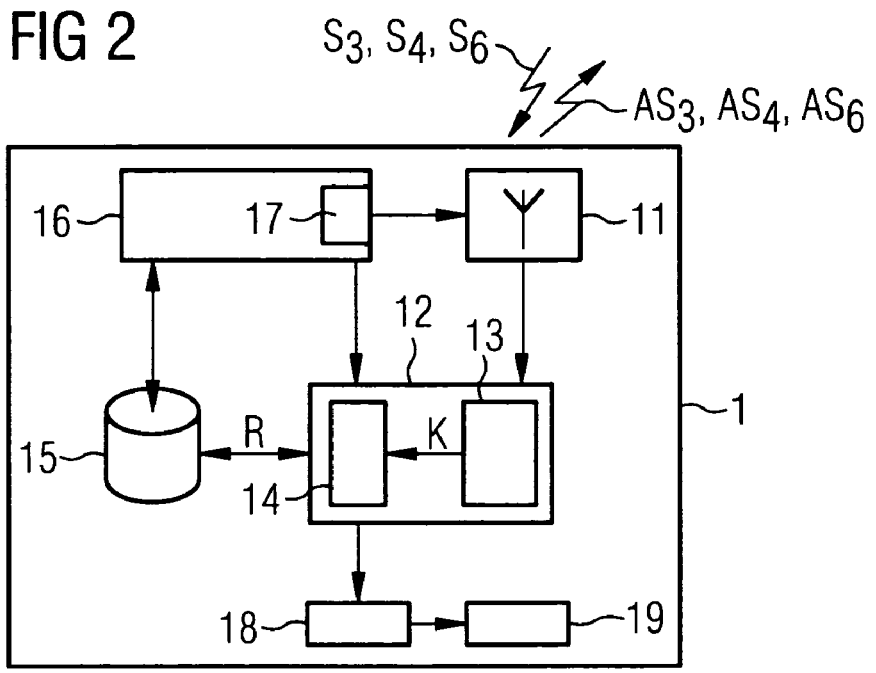
FIG. 2 shows a schematic diagram of the components used to protect a medical device in the relevant device.

This is shown in FIG. 2 for the X-ray detector 1. FIG. 2 only shows the elements required for the claimed protection of the detector 1. The detector 1 of course also has all the other elements it requires for its use as a detector in the required manner.

As well as the transmit/receive unit 11, the detector 1 also has a selection unit 16, an evaluation unit 12 with a combination unit 13 and a comparison unit 14 as well as a memory unit 15 with ID stored therein for the different devices 2, 3, 4, 5, 6, 7, 8, 9 within the protection system 20, which can be used to protect the X-ray detector 1. The detector 1 also has an activation unit 18 and an alarm arrangement 19.

To a large extent these elements, in particular the evaluation unit 12 with the combination unit 13 and the comparison unit 14, the activation unit 18 and the selection unit 16 can be implemented in the form of software on a suitable microprocessor within the detector 1. If the detector 1 has a freely programmable microprocessor anyway for other purposes, the components can also be implemented on this microprocessor. In other words a microprocessor otherwise used for imaging can also be used for the claimed purpose. Memory unit components can also be used, if a corresponding amount of capacity is reserved for the claimed application.

A specific unique ID is assigned to each of the different devices and components 2, 3, 4, 5, 6, 7, 8, 9 within the protection system 20. These IDs are stored in the memory unit 15 of the detector 1. So that the detector 1 can identify whether it is still within the permitted location area, different devices 2, 3, 4, 5, 6, 7, 8, 9 available in the protection system 20 are regularly selected by a selection unit 16 by means of a random method.

In the exemplary embodiment shown in FIG. 1 the check monitor 6, the X-ray emitter 3 and the screen wall device 4 are selected. The random selection of the different devices which have to respond ensures that the entire method is largely proof against snooping and that it is not possible to intercept the scans or protection signals by radio and then transmit signals in a specific manner to simulate a secure environment for the device to be protected.

Corresponding prompt signals $AS_3, AS_4, AS_6$ are then generated by a prompt unit 17 and transmitted via the transmit/receive module 11 to the respective devices 3, 4, 6. The devices 3, 4, 6 respectively receive the prompt signal $AS_3$, $AS_4, AS_6$ with their transmit/receive modules and send back a protection signal $S_3, S_4, S_6$. This protection signal $S_3, S_4, S_6$ is then received by the transmit/receive module 11 of the detector 1 and fed to the evaluation unit 12. The protection signals $S_3, S_4, S_6$ are then combined to form a combination value K in a combination unit 13 and this combination value K is then forwarded to a comparison unit 14. A comparison with a reference value R then takes place in this comparison unit 14.

This reference value R is also stored in the memory unit 15 for every combination of device signals for example. Alternatively the same arithmetic rule can be used by the combination unit 13 to combine the IDs of the requested devices 3, 4, 6 stored in the memory unit correspondingly to obtain the reference value.

If the combination value K determined corresponds to the reference value R, it is clear that the correct devices 3, 4, 6 have sent back their protection signals $S_3, S_4, S_6$. It can therefore be assumed that the detector 1 to be protected is still in the permitted location area.

Correspondingly it is ensured by the activation unit 18 based on the result from the comparison unit 14 that the detector 1 is released or remains in a released operating state. If a negative result were determined, this would mean that the correct protection signals were not received. In this case the detector 1 switches to a lock-out operating state, if it is not already in such an operating state.

An alarm can also be activated via an alarm arrangement 19. To prevent an alarm being activated in error, it is possible to block the detector before an alarm is activated and carry out a new verification immediately, only activating the alarm in the case of a second negative result.

In particular if a number of different components are scanned, it is also possible to provide a specific confidence range. Not all the components then have to respond definitively. Instead errors are also permitted within specific limits. This reduces the likelihood of the alarm being activated in error or the detector not being able to be given, even though only minor transmission errors have occurred during transmission of the protection signals.

Such a verification preferably takes place at regular time intervals. However a verification takes place at the latest when the detector is to be brought into operation. Alternatively it is also possible to provide the detector with a sort of movement alert and to transmit corresponding prompt signals for protection signals when the detector is moved.

In principle it is possible for each of the devices 2, 3, 4, 5, 6, 7, 8, 9 belonging to the system 20, such as the detector 1, to have corresponding protection elements and therefore also to be protected by the other devices. In this preferred instance there is mutual protection of the most diverse devices 1, 2, 3, 4, 5, 6, 7, 8, 9 in that each of the devices 1, 2, 3, 4, 5, 6, 7, 8, 9 transmits a corresponding protection signal $S_1$, $S_2$, $S_3$, $S_4$, $S_5$, $S_6$, $S_7$, $S_8$, $S_9$.

Figure 3:
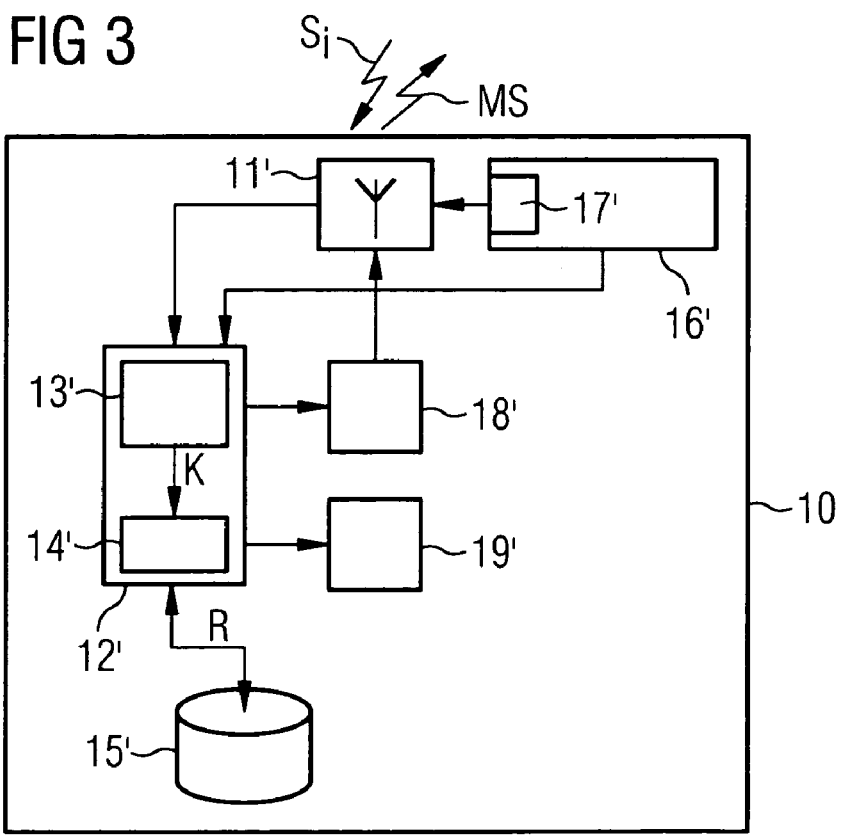
FIG. 3 shows a schematic diagram of the components in a central protection arrangement for use in the claimed method.

Alternatively protection can be achieved with the aid of a central protection arrangement 10. This is shown here as a component 10 within the image processor 7. The structure of such a central protection arrangement 10 is shown in FIG. 3.

The central protection unit 10 also has a transmit/receive module 11' and an evaluation unit 12' with a combination unit 13' and a comparison unit 14'. The central protection arrangement 10 also has a memory unit 15' containing the IDs of the different devices 1, 2, 3, 4, 5, 6, 7, 8, 9 used in the system. The central protection arrangement 10 also has a selection unit 16' with a prompt unit 17', an activation signal generator 18' and an alarm arrangement 19'.

The mode of operation of this central protection arrangement 10 is similar to the mode of operation of the protection elements in the detector 1 according to FIG. 2.

The central protection arrangement 10 is hereby responsible for selecting the devices 1, 2, 3, 4, 5, 6, 7, 8, 9, having respectively to transmit the protection signals for a device to be protected, as well as the evaluation of the received protection signals.

It also ensures activation of the required operating states of the individual devices to be protected. To this end the selection unit 16' first selects a number of devices, which are to send a protection signal to a specific other device to be protected. Corresponding prompt signals are generated accordingly in the prompt unit 17' and transmitted via the transmit/receive module 11'. The device to be protected then only has to receive the protection signals $S_i$(i=1, . . . ,9) and can then evaluate these and compare them with a reference signal R also received by the central protection arrangement, which was generated according to the selected devices.

Alternatively it is also possible for the devices to be protected each only to have suitable means for forwarding the received protection signals $S_i$ to the central protection arrangement 10. This latter arrangement then receives the protection signals $S_i$ with its transmit/receive module 11 and forwards them to the evaluation module 12'. The different protection signals $S_i$ are combined to give a combination value K in the combination unit 13'. They are then compared in a comparison unit 14' with a reference value R, which is in turn stored in the memory unit 15' for example. In the event of a negative result a signal is sent to a central alarm arrangement 19', which for example outputs an alarm signal locally and also signals to the doors of the hospital, etc. that a device may be being misappropriated.

An activation signal generator 18' is also used to output a corresponding activation signal MS and send it via the transmit/receive module 11' to the device to be protected. This then switches to the required operating state, for example a lockout state. Alternatively it is also possible, if the result is positive, for the activation signal generator 18' to generate a corresponding activation signal MS, which ensures that the device to be protected is first released.

The claimed system can therefore be used in a relatively simple manner to protect a number of components within an extensive institution—for example a hospital—in that simple use is made of the fact that the individual devices protect each other and it is therefore signaled to each device whether it is still in the permitted environment.

If a device is to be moved out of the environment in an authorized manner, notification of this must be given first to the device, for example via a central protection arrangement or by an input at the device itself. This should preferably be done such that the respective person wishing to "book" the device out of the protection system has to be appropriately authenticated in respect of the device or protection system.

The embodiments of the invention described above only represent exemplary developments. A number of further embodiments of the invention are also included in the idea of the invention, even if they have not been specifically described in the above embodiments. In particular the most diverse combinations of the described variants are possible.

The invention claimed is:

1. A method for protecting a medical device against unauthorized removal from a predefined location area, comprising:

transmitting protection signals by the medical device;

evaluating received protection signals received by the medical device from a plurality of selected devices; and activating a specific operating state of the medical device based on the evaluation, wherein the evaluation of the received protection signals includes determining a combination value based on the received protection signals received from the plurality of selected devices using a combination rule.

2. The method according to claim 1, wherein the received protection signals comprise an ID uniquely assigned to a corresponding transmitting device.

3. The method according to claim 2, wherein the ID is obtained based on randomly occurring device features of the transmitting device.

4. The method according to claim 1, wherein the medical device transmits a prompt signal for initiating a transmission of at least one protection signal by at least one other device different from the medical device.

5. The method according to claim 4, wherein the prompt signal is transmitted to the group of previously selected devices.

6. The method according to claim 4, wherein the at least one other device is randomly determined.

7. The method according to claim 1, wherein the evaluation of the received protection signals further includes comparing an individual protection signal or a combination value derived from a plurality of received protection signals to a reference value.

8. The method according to claim 1, wherein the medical device is released for use if evaluation of the protection signals or the evaluation of the received protection signals corresponds to a positive evaluation result.

9. The method according to claim 1, further comprising triggering an alarm if evaluation of the protection signals or the evaluation of the received protection signals corresponds to a negative evaluation result.

10. The method according to claim 1, wherein the medical device transmits the received protection signals to a central protection device, the central protection device configured to:
  perform the evaluation of the received protection signals, and
  release the medical device for use or to trigger an alarm based on the evaluated received protection signals.

11. The method according to claim 10, wherein
  a combination value is determined from the received protection signals received from the group of devices, and
  the central protection device is further configured to:
  release the group of devices for use or to trigger the alarm related to the group of protection devices.

12. The method according to claim 10, wherein
  the central protection device transmits a device information signal to the medical device, the device information signal comprising information on the group of devices.

13. The method according to claim 10, wherein the central protection device transmits a reference value to the medical device for comparing the reference value to at least one received protection signal or to the combination value derived from a plurality of received protection signals.

14. The method according to one of claims 1, wherein the medical device comprises a mobile X-ray detector.

15. A system for protecting a medical device against unauthorized removal from a predefined location area, comprising:
  the medical device;
  a plurality of further medical devices present in the predefined location area, the further medical devices each including a transmitter for transmitting protection signals to the medical device or a receiver for receiving protection signals from the medical device;
  a transmitter connected to the medical device for transmitting protection signals or a receiver connected to the medical device for receiving protection signals transmitted by the further medical devices;
  an evaluation unit for evaluating the protection signals transmitted by the medical device or for evaluating the protection signals received by the medical device and transmitted by the further medical devices;
  an activation unit connected to the medical device for activating a specific operating state of the medical device based on the evaluation of the protection signals,
  wherein the evaluation unit comprises a combination unit for determining a combination value derived from a plurality of protection signals received by the medical device based on a combination rule.

16. The system according to claim 15, wherein the evaluation unit is integrated into the medical device.

17. The system according to claim 15, wherein the medical device or the further medical devices include a transmitter for forwarding protection signals received by the medical device respectively by the further medical devices.

18. The system according to claim 17, further comprising a central protection device, the central protection device comprising:
  a receiver for receiving the forwarded protection signals;
  a central evaluation unit for evaluating the forwarded protection signals;
  a transmitter for transmitting an activation signal to the medical device based on the evaluation of the protection signals, the activation signal adapted to activate the specific operating state; and
  an alarm unit for triggering an alarm based on the evaluation of the protection signals.

19. The system according to claim 15, wherein the medical device includes a transmitter for transmitting a prompt signal to at least one of the further medical devices, the prompt signal triggering the at least one of the further medical devices to transmit a protection signal.

20. The system according to claim 15, wherein the evaluation unit further comprises a comparison unit for comparing a protection signal or the combination value derived from a plurality of protection signals to a reference value.

21. A medical device, comprising:
  a transmitter for transmitting protection signals;
  a receiver for receiving protection signals transmitted by a further medical device, the medical device and further medical device present in a predefined location area;
  an evaluation unit for evaluating The protection signals received by the medical device;
  a further transmitter for forwarding the protection signals transmitted by the further medical device;
  a further receiver for receiving an activation signal; and
  an activation unit for activating a specific operating state of the medical device based on the evaluation of The protection signals or on the received activation signal,
  wherein the evaluation unit comprises a combination unit for determining a combination value derived from a plurality of protection signals received by the medical device based on a combination rule.

* * * * *